United States Patent [19]

Polisson

[11] Patent Number: 5,098,839
[45] Date of Patent: Mar. 24, 1992

[54] **TYPE II RESTRICTION ENDONUCLEASE OBTAINABLE FROM *PSEUDOMONAS ALCALIGENES* AND A PROCESS FOR PRODUCING THE SAME**

[75] Inventor: Carol Polisson, Reading, Mass.

[73] Assignee: New England Biolabs, Inc., Beverly, Mass.

[21] Appl. No.: 521,540

[22] Filed: May 10, 1990

[51] Int. Cl.$^5$ .......................... C12N 9/22; C12P 19/34
[52] U.S. Cl. ........................................ 435/199; 435/91
[58] Field of Search ................................. 435/199, 91

[56] References Cited

PUBLICATIONS

Roberts, R. J. (1989), Nucl. Acids Res. 17 (suppl.), r347–r389.
Endov et al., J. Mol. Biol., 112:521 (1977).
Waalwijk et al., Nucleic Acids Res., 5:3231 (1978).
Gingeras et al., Proc. Natl. Sci. Acad., U.S.A., 80:402 (1983).
Lunnen et al., Gene 74:25–32 (1988).

Primary Examiner—Charles L. Patterson
Attorney, Agent, or Firm—David G. Conlin; Gregory D. Williams; David S. Resnick

[57] ABSTRACT

The present invention provides a novel Type II restriction endonuclease obtainable from *Pseudomonas alcaligenes*. The endonuclease known as PacI, recognizes the following nucleotide sequence and has a cleavage point indicated by the arrows:

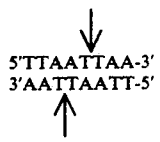

Also described is a process for obtaining PacI from *P. alcaligenes*.

6 Claims, 1 Drawing Sheet

TYPE II RESTRICTION ENDONUCLEASE OBTAINABLE FROM *PSEUDOMONAS ALCALIGENES* AND A PROCESS FOR PRODUCING THE SAME

BACKGROUND OF THE INVENTION

The present invention relates to a new Type II restriction endonuclease, PacI, obtainable from *Pseudomonas alcaligenes*, and to process for producing the same.

Many bacteria contain systems which guard against invasion of foreign DNA. Bacterial cells contain specific endonucleases that make double-strand scissions in invading DNA unless the DNA has been previously modified, usually by the appropriate corresponding DNA methylase. The endonuclease with its accompanying methylase is called a restriction-modification system (hereinafter "R-M system"). The principle function of R-M systems is thus defensive: they enable bacterial cells to resist infections by bacteriophage and plasmid DNA molecules which might otherwise parasitize them.

Bacteria usually possess only a small number of restriction endonucleases per species. The endonucleases are named according to the bacteria from which they are derived. Thus, the species *Haemophilus aegyptius*, for example synthesizes three different restriction endonucleases, named HaeI, HaeII, and HaeIII. These enzymes recognize and cleave the sequences (AT)GGCC(AT), PuGCGCPy and GGCC respectively. *Escherichia coli* RY13, on the other hand, synthesizes only one restriction endonuclease, Eco RI, which recognizes the sequence GAATTC.

Restriction endonucleases, the first component of R-M systems, have been characterized primarily with respect to their recognition sequence and cleavage specificity because of their practical use for molecular dissection of DNA. The majority of restriction endonucleases recognize sequences 4–6 nucleotides in length. More recently, recognition endonucleases having recognition sequences of 7–8 nucleotides in length have been found. Most, but not all, recognition sites contain a dyad axis of symmetry, and in most cases, all the bases within the site are uniquely specified. This symmetrical relationship in the recognition sequence of restriction endonucleases has been termed "palindromes". Some restriction endonucleases have degenerate or relaxed specificities in that they can recognize multiple bases at the same positions. HaeIII, which recognizes the sequence GGCC is an example of restriction endonuclease having a symmetrical relationship, while HaeII, which recognizes the sequence PuGCGCPy, typifies restriction endonucleases having a degenerate or relaxed specificity. Endonucleases with symmetrical recognition sites generally cleave symmetrically within or adjacent to the recognition site, while those that recognize asymmetric sites tend to cut at distance from the recognition site, typically from about 1–18 base pairs away from the site.

The second component of bacterial R-M systems are the modification methylases. These enzymes are complementary to restriction endonucleases and provide the means by which bacteria are able to protect their own DNA and distinguish it from foreign, infecting DNA. Modification methylases recognize and bind to the same nucleotide recognition sequence as the corresponding restriction endonuclease, but instead of breaking the DNA, they chemically modify one or other of the nucleotides within the sequence by the addition of a methyl group. Following methylation, the recognition sequence is no longer bound or cleaved by the corresponding restriction endonuclease. The DNA of a bacterial cell is always fully modified, by virtue of the activity of its modification methylase and it is therefore completely insensitive to the presence of the endogenous restriction endonuclease. It is only unmodified, and therefore identifiably foreign, DNA that is sensitive to restriction endonuclease recognition and attack.

More than 1000 different restriction endonucleases have been isolated from bacterial strains, and many share common specificities. Restriction endonucleases which recognize identical sequences are called "isoschizomers". Although the recognition sequences of isoschizomers are the same, they may vary with respect to site of cleavage (e.g., XmaI V. SmaI Endow, et al., *J. Mol. Biol.* 112:521 (1977); Waalwijk, et al., *Nucleic Acids Res.* 5:3231 (1978)) and in cleavage rate at various sites (XhoI v. Pae R7I Gingeras, et al., *Proc. Natl. Acad. Sci U.S.A.* 80:402 (1983)).

Specific Type II restriction endonucleases are already known for numerous DNA sequences, however, a large number of restriction enzymes with diversified enzymatic characteristics are necessary for successful genetic manipulation. In particular, restriction endonucleases that require eight specific nucleotides in their recognition sequence are quite rare. In fact, to date only three have been identified, NotI (GCGGCCGC), SfiI (GGCCNNNNNGGCC), and FseI (GGCCGGCC).

Accordingly, there is a continued need for Type II restriction endonucleases which recognize novel DNA sequences, and in particular, those which recognize eight nucleotides recognition sequences.

SUMMARY OF THE INVENTION

In accordance with the present invention, there is provided a novel restriction endonuclease obtainable from the bacterium *Pseudomonas alcaligenes* endonuclease, hereinafter referred to as "PacI", which endonuclease:

(1) recognizes the base sequence in a double-stranded DNA molecule as shown below,

(wherein A and T represent adenine and thymine, respectively);

(2) cleaves said sequence in the phosphodiester bonds between T and T as indicated with the vertical arrows; and (3) cleaves double-stranded Adeno2, T7 and M13mp18 DNA in one position, while not cleaving pBR322, phiXI74, pUC19, SV40 or lambda DNAs.

The present invention further relates to a process for the production of the novel restriction endonuclease PacI which comprises culturing *Pseudomonas alcaligenes* under conditions suitable for expressing PacI, collecting the cells, obtaining a cell-free extract therefrom and separating and collecting the restriction endonuclease PacI from the cell-free extract.

DETAILED DESCRIPTION OF THE INVENTION

Figure 1:
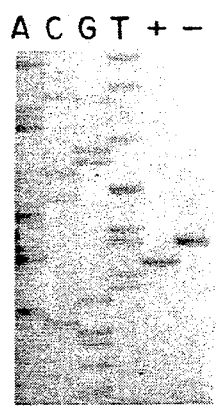
FIG. 1—Site of cleavage determination for PacI. + indicates addition of Klenow fragment after cleavage of Pac I. − indicates no treatment with Klenow subsequent to Pac I cleavage.

In accordance with the present invention, PacI is obtained by culturing *Pseudomonas alcaligenes* strain NEB 585 and recovering the enzyme from the cells.

*Pseudomonas alcaligenes* strain NEB 585 was isolated from a water sample obtained from a bayou located in Louisiana in 1989. The sample was returned to New England Biolabs and plated on LB agar. Selected colonies were picked and plate purified. Purified samples were assayed for endonuclease activity in accordance with the technique described by Schildkraut in *Genetic Engineering Principles and Methods*, (1984) Setlow, J. K. et al., eds., Plenum Publishing, Vol. 6, pg. 117, the disclosure of which is hereby incorporated by reference. One sample identified as *Pseudomonas alcaligenes* NEB 585 contained the novel restriction endonuclease PacI.

A sample of *Pseudomonas alcaligenes* strain NEB 585 was deposited at the American Type Culture Collection (ATCC) on May 7, 1990 and bears Accession No. 55044.

For recovering the enzyme of the present invention, *P. alcaligenes* may be grown using any suitable technique, for example, *P. alcaligenes* may be grown in a media comprising tryptone, yeast extract and NaCl (pH 7.2), and incubated at 30° C. with agitation and aeration. Cells in the late logarithmic stage are collected using centrifugation and stored frozen at −70° C.

After the cells are harvested and frozen, the enzyme can be isolated and purified from the frozen cell paste by using conventional enzyme purification methods. For example, the obtained cell paste is thawed and suspended in a buffer solution and subjected to treatment to allow extraction of the enzyme by the buffer solution, such treatment includes sonication, high pressure dispersion, or enzymatic digestion. The cell residue is then removed by centrifugation, and the supernatant containing the new enzyme can be purified by ion-exchange chromatography, using for example phosphocellulose or DEAE-cellulose, molecular sieve chromatography and affinity chromatography, using for example heparin agarose or DNA-cellulose, or a combination of these methods, to produce the enzyme of the present invention.

The enzyme of the present invention along with its corresponding DNA methylase may also be obtained using recombinant DNA techniques, such as the methylase selection technique disclosed by Wilson, et al., EPO Publication No. 019413, the disclosure of which is herein incorporated by reference. For example, the methylase selection technique can be carried out in three steps. First, DNA from a bacterial strain encoding an R-M system is purified, partially digested with cloning endonucleases, and then ligated to a cleaved, dephosphorylated plasmid vector. The ligated DNA is transformed into *E. coli*; the transformants are pooled and the populations of plasmids are purified to form libraries. Next, the libraries are digested with a selecting endonuclease, one which can be blocked by the specific modification that the methylase confers. The digests are transformed back into *E. coli* to recover undigested molecules. The transformants can be screened immediately, or pooled and the plasmids cycled through further rounds of purification and selection. Finally, individual transformants are collected and mini-preparations are made of their plasmids. The plasmids are analyzed for resistance to digestion by the endonuclease of interest and for possession of common inserts. (The methylase gene will be encoded by at least one fragment, which will generally be present in all bona fide methylase clones.) Cell extracts are prepared from positive candidates and assayed in vitro for methyltransferase activity and endonuclease activity.

However, a number of R-M systems have been found to be more complex and therefore more difficult to obtain using recombinant DNA techniques and require modification of the above-described approach to cloning R-M systems. See Lunnen, et al., (1988) *Gene* 74:25–32, the disclosure of which is hereby incorporated by reference. For example, in some systems, the methylase and endonuclease genes may not be linked or the endonuclease used to fragment the bacterial DNA may cut either or both of the R-M genes. In other systems, such as BamHI and DdeI, the methylase may not protect sufficiently against digestion by the corresponding endonuclease, either because of the inefficient expression in the transformation host, or because of the inherent control mechanism for expression of the methylase and endonuclease genes, or for unknown reasons. Modification has also been found to be harmful to the host cell chosen for transformation. Another difficulty in cloning R-M systems is that the endonuclease sought to be cloned may not be available in sufficient purity or quantity for methylase selection. Finally, in many systems, difficulties are encountered in expressing the endonuclease gene in a transformation host cell of a different bacterial species.

The recognition sequence of the endonuclease of the present invention, PacI can be determined by double-digesting Adeno2, T7 and M13mp18 DNA with the restriction endonuclease of the present invention and a restriction enzyme which cleaves the test DNA at known sites. The size of the DNA restriction fragments obtained can be determined using agarose gel electrophoresis. Using this technique the following results were obtained:

(a) The single recognition sequence of PacI on Adeno2 DNA was mapped to approximately 28,500 base pairs by analysis against ClaI, NdeI, and SpeI cleaved Adeno2 DNA. The sequence 5'TTAATTAA3' occurs at only one position 28,618 base pairs.

(b) The single recognition sequence of PacI on T7 DNA was mapped to approximately 27,000 base pairs by analysis against AlwI, BanII, BclI, BglII, BssHII, BstEII, EcoNI, MluI, NcoI, NheI, SfiI, and StuI cleaved T7 DNA. The sequence 5'TTAATTAA3' occurs at only one position 27,222 base pairs.

(c) The single recognition sequence of PacI on M13mp18 DNA was mapped to approximately position 4096 base pairs by analysis against SnaBI, BsmI, and BglII cleaved M13mp18 DNA. The sequence 5'TTAATTAA3' occurs at only one position 4132 base pairs.

(d) There is no observed cleavage of pBR322 DNA, pUC19 DNA, phiX174 DNA, SV40 DNA or lambda DNA. The sequence 5'TTAATTAA3' does not occur within the sequence of these molecules.

As is shown below in Table 1, the number and sizes of the fragments generated by digestion with PacI on eight DNA molecules match the computer predicted number and sizes of the fragments that would be generated by cleavage at the sequence 5'TTAATTAA3'.

From the above data, it was thus concluded that PacI recognizes the sequence 5'TTAATTAA3'.

TABLE 1

| | Number of Experimental Observed Cleavage Sites | Number of Cleavage Sites Obtained by Computer Search | Experimentally Derived Location of Recognition Sequence | Location of TTAATTAA Obtained by Computer Search |
|---|---|---|---|---|
| Adeno2 | 1 | 1 | 28,500 | 28,618 |
| T7 | 1 | 1 | 27,000 | 27,222 |
| M13mp18 | 1 | 1 | 4,096 | 4,132 |
| pBR322 | 0 | 0 | — | — |
| PhiX174 | 0 | 0 | — | — |
| pUC19 | 0 | 0 | — | — |
| SV40 | 0 | 0 | — | — |
| Lambda | 0 | 0 | — | — |

The point of cleavage on the recognition sequence of the endonuclease of the present invention can be determined by using dideoxy sequencing (Sanger, F., et al., PNAS (1977) 74:5463–5467) to analyze the terminal base sequence obtained by cleaving pvPACI-11IB, a pBR322 derived double-stranded plasmid, with the enzyme of the present invention. pvPACI-llB is formed using standard techniques to insert an 8-nucleotide linker comprising the PacI recognition sequence, 5'TTAATTAA3', into the PVUII site of pBR322 (ATCC #37017). Using the technique described above and further exemplified in Example II, it was concluded that the PacI cleavage position is between the fifth and sixth nucleotides, T and T, in its recognition sequence which results in a 3' two-base extension as shown below,

wherein the cleavage position is defined with the vertical arrows.

The enzyme of the present invention has the following additional properties:

(a) NaCl Concentration: The optimal salt concentration was at 0 mM NaCl, the relative activity being 33% for 100 and 150 mM NaCl. Activity was higher at a concentration of 0–5 mM NaCl than at a concentration of 150 mM NaCl.

(b) Temperature: Activity was higher at 37° C. than at 25° C.

(c) pH: The activity was higher at pH 7.0 than pH 8.0

The following examples are given to illustrate embodiments of the present invention as it is presently preferred to practice. It will be understood that the examples are illustrative, and that the invention is not to be considered as restricted except as indicated in the appended claims.

EXAMPLE I

*Pseudomonas alcaligenes* strain NEB 585 (ATCC #55044) was grown in media consisting of 10 g/l tryptone, 5 g/l yeast extract, 5 g/l NaCl (adjusted to pH 7.2). The cells were incubated at 30° C. until late logarithmic stage with aeration and agitation. The cells were harvested by centrifugation and stored frozen at −70° C.

110 g of the cells obtained above were suspended in three volumes of buffer A (0.3 NaCl, 10 mM KPO4, 0.1 mM EDTA, 10 mM β-ME, pH 6.0). Phenylmethylsulfonyl fluoride was added to 25 μg/ml and the cells were sonicated until approximately 46 mg of protein/g cell was released. The lysate was centrifuged at 4° C. for 70 minutes at 17,000 rpm (Beckman JA17 rotor).

The supernatant obtained was ultracentrifuged at 4° C. for one hour at 40,000 rpm (Beckman Ti50.2 rotor). The supernatant solution was loaded onto a DEAE-Sepharose column (138 mls). The flow-through was collected and glycerol was added to 5%. The solution was dialyzed for four hours against 4 liters of buffer B (0.15 M NaCl, 10 mM KP04, 0.1 mM EDTA, 10 mM β-ME, 5% glycerol, pH 6.0).

The dialyzate was applied to a heparin-Sepharose column (93 mls). The column was then washed with 200 mls buffer B and eluted with a linear gradient of 0.15 to 1.0 M NaCl in buffer B. The fractions obtained were tested for PacI activity (10 minute incubation) and exonuclease activity, as described below. Fractions eluting at 0.5 mols/l NaCl possessed PacI activity and were collected. Exonuclease activity was detected immediately before and on top of PacI activity.

To the fractions with PacI activity, buffer B without salt was added until conductivity equaled that of 0.15M NaCl, the volume was 125 mls. This solution was loaded onto a phosphocellulose column (27 mls) and the column was washed with 50 mls of buffer B and the enzyme was eluted with a 270 ml gradient of 0.15 to 1.0M NaCl in buffer B. The fractions obtained were tested for PacI and exonuclease activity, as described below. Exonuclease activity eluted on top of PacI activity.

The fractions possessing peak PacI activity eluted at between 0.4 and 0.45 mol/l NaCl were pooled and loaded immediately onto a G-75 Sephadex column (2.5×96 cm). The column was eluted slowly (one drop/15 seconds) with buffer C (0.15M NaCl, 5% glycerol, 10 mM β-ME, 10 mM KP04, 0.1 mM EDTA, pH 6.0). The fractions obtained were assayed for PacI and exonuclease activity. Exonuclease activity eluted with PacI activity.

The fractions were collected, assayed and fractions eluting between 220 and 245 mls containing PacI activity were pooled and dialyzed against 4 liters of buffer D (5% glycerol, 10 mM β-ME, 50 mM NaCl, 20 mM KPO4, pH 6.0) for four hours. The dialyzate was loaded onto a heparin-TSK HPLC column. The enzyme activity was eluted with a 52 ml linear gradient of 50 mM NaCl to 0.6M NaCl in buffer D. The fractions were collected and 2 μl of each fraction was assayed for PacI activity (15 minute incubation) and exonuclease activity. Peak PacI activity was found in fractions eluting between 0.37 and 0.4 mol/l NaCl. Peak exonuclease activity was found at fractions eluting between 0.4 and 0.43 mol/l NaCl.

Fractions possessing peak PacI activity were pooled. Equal amounts of 100% glycerol was added to the pooled fraction and BSA was added to 200 μg/ml. The enzyme obtained was substantially pure and substantially free from any nonspecific endonuclease and exonuclease activity. The enzyme was stored in 50% glycerol, 10 mM β-ME, 190 mM NaCl, 20 mM KP04, pH6.0 at −20° C.

Activity Determination

PacI activity: A 2 μl sample of the fraction to be tested was added to 25 μl of the substrate solution (10 mM Tris-HCl, 10 mM MgCl$_2$, 1 mM DTT, 100 μg/ml BSA, pH 6.0 containing 0.5 μg PstI linerized pvPACI-IIB DNA). The enzymatic reaction was incubated at 37° C. for the time indicated, 10 or 15 minutes. The reaction was terminated by adding 7.0 μl of a Stop solution (50% glycerol, 50 mM EDTA pH 8.0, and 0.02% Bromophenol Blue). The reaction mixture was applied to a 1.0% agarose gel and electrophoresed. The bands obtained were identified in comparison with DNA length standards.

Exonuclease activity: A 2 μl sample of the protein solution was added to 50 μl of 10 mM Tris-Hcl, 10 mM MgCl2, 1 mM DTT, 100 μg/ml BSA, pH 6.0, containing 25 μg/ml $^3$H-DNA. The reaction was incubated at 37° C. for one hour.

Unit Definition: One unit of PacI completely cleaves 1 μg of pvPACI-IIB DNA within one hour at 37° C.

Optimum Buffer Conditions: For optimum PacI activity the following buffer was used: 10 mM Tris-Hcl, 10 mM MgCl$_2$, 1 mM DTT, 100 μg/ml BSA, pH 7.

EXAMPLE II

Determination of the PacI Cleavage Site

Denaturing the pvPACI-11B

3 μg of pvPACI-llB purified plasmid DNA was dissolved in a total of 20 μl dH20 in a 1.5 ml eppendorf tube. 2 μl of 2M NaOH, 2 mM EDTA was added and the solution incubated 5 minutes at room temperature. 7 μl dH20 (4° C.), 6 μl 3M NaAcetate pH 5.0 (4° C.) and 75 μl ETOH (4° C.) were added rapidly. The solution was immediately placed in a dry ice/2-propanol bath for 15 minutes to precipitate the DNA. The DNA was pelleted by centrifugation for 10 minutes in an eppendorf centrifuge, 95% of the supernatant was removed by aspiration, 300 μl of 70% ETOH/30% dH20 was added and the solution centrifuged for 5 minutes, followed by removal of approximately 95% of the supernatant. The DNA pellet was then completely dried in a speed-vac apparatus for 10 minutes.

Sequencing Reactions

An oligonucleotide primer (5'CGCTTACAGACAAGCTGTG3') was synthesized, using standard techniques, to sequence through the PacI site of pvPACI-11B.

To the dried pellet were added 13.5 μl dH20, 2.25 μl 10 X sequencing buffer (75 mM Tris pH 7.6, 55 mM DTT, 50 mM MgCl2), and 1.5 μl of 1.0 μm primer solution. The solution was incubated at 37° C. for 30 minutes. 3 μl of [alpha-$^{35}$S] dATP at 800 Ci/mmole, 10 mCi/ml was added. 1.5 μl (7.5 units) Klenow fraqment DNA polymerase (obtained from New England Biolabs, Inc.) was added. This solution was called the TPK mixture. 3.2 μl of the TPK mixture was aliquoted into 3 μl of the deoxy/dideoxy nucleotide reaction mixtures (obtained from New England Biolabs, Inc.) for the A, C, G and T sequencing reactions. The remaining TPK mixture was added to 9 μl of the A sequencing reaction mix which contained no dideoxy nucleotides to create a labeled strand of DNA extending through the PacI recognition site. The reactions were incubated 15 minutes at 37° C. 1 μl of dNTP chase solution (obtained from New England Biolabs, Inc.) was added to the A, C, G and T reactions. 3 μl chase was added to the extension reaction. The reactions were incubated an additional 15 minutes at 37° C. 6 μl stop solution (obtained from New England Biolabs, Inc.) was added to the A, C, G and T sequencing reactions and these were stored at −20° C. until run on a sequencing gel. The extension reaction was incubated at 70° C. for 25 minutes to inactivate the DNA polymerase (Klenow), then incubated at room temperature for 10 minutes. 9 μl of the extension reaction was placed in one 0.5 ml eppendorf tube and 6 μl were placed in a second tube. To the 9 μl tube was added 1 μl (approximately 0.75 units) PacI endonuclease. The reaction was mixed and 2 μl were transferred to the second tube. The enzyme reactions were incubated at 37° C. for 30 minutes. Following digestion 4 μl of the reactions were removed and mixed with 5 μl stop solution. To the remaining 4 μl was added 0.25 μl (1.25 units) Klenow fragment and the reaction incubated at room temperature for 12 minutes, after which 5 μl of stop solution was added. The enzyme digest reactions were also stored at −20° C. prior to running the gel. The reaction products were electrophoresed on an 8% bis-acrylamide sequencing gel, with the PacI digestion of the extension reaction next to the set of sequencing reactions produced from the same primer (see FIG. 1).

Digestion of the extension reaction product with PacI endonuclease produced a band which co-migrated with the third T of the PacI recognition sequence 5'TTAATTAA3'. Treatment with Klenow fragment following PacI digestion produced a fragment which co-migrated with the 5'A in the PacI recognition sequence of 5'TTAATTAA3'. These results indicated that the PacI cleavage site was between the fifth and sixth nucleotides, T and T, in its recognition sequence 5'TTAAT/TAA3' and thus produced a two-base 3' extension.

What is claimed is:

1. A substantially pure Type II restriction endonuclease obtainable from *Pseudomonas alcaligenes* recognizing the following base sequence in double-stranded deoxyribonucleic acid molecules:

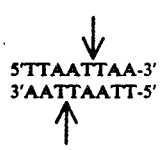

and having a cleavage position defined by the arrows.

2. The Type II restriction endonuclease of claim 1, having a greater activity at 37° C. than at 25° C.

3. The Type II restriction endonuclease of claim 1, cleaving double-stranded deoxyribonucleic acid Adeno2, T7 and M13mp18 in one position.

4. The Type II restriction endonuclease of claim 1, having greater activity at pH 7.0 than pH 8.0.

5. The Type II restriction endonuclease of claim 1, having greater activity at a NaCl concentration of 0 to 5 mM than at a concentration of 150 mM.

6. A method for obtaining the Type II restriction endonuclease of claim 1, comprising cultivating a sample of *Pseudomonas alcaligenes* under conditions favoring production of said endonuclease and separating said endonuclease therefrom.

* * * * *